(12) United States Patent
Rini et al.

(10) Patent No.: US 11,744,949 B2
(45) Date of Patent: Sep. 5, 2023

(54) SYSTEM AND METHOD FOR DETECTING APPLIED FORCE DURING INJECTION

(71) Applicant: Becton, Dickinson and Company, Franklin Lakes, NJ (US)

(72) Inventors: Christopher Rini, Raleigh, NC (US); Bruce Roberts, Franklin Lakes, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 148 days.

(21) Appl. No.: 16/635,460

(22) PCT Filed: Aug. 29, 2018

(86) PCT No.: PCT/US2018/048558
§ 371 (c)(1),
(2) Date: Jan. 30, 2020

(87) PCT Pub. No.: WO2019/046436
PCT Pub. Date: Mar. 7, 2019

(65) Prior Publication Data
US 2021/0100954 A1    Apr. 8, 2021

Related U.S. Application Data

(60) Provisional application No. 62/553,004, filed on Aug. 31, 2017.

(51) Int. Cl.
*A61M 5/20* (2006.01)

(52) U.S. Cl.
CPC ......... *A61M 5/20* (2013.01); *A61M 2205/332* (2013.01); *A61M 2205/52* (2013.01);
(Continued)

(58) Field of Classification Search
CPC ............ A61M 5/20; A61M 2005/2006; A61M 2005/2013; A61M 2005/208;
(Continued)

(56) References Cited

U.S. PATENT DOCUMENTS 8,641,672 B2 *   2/2014   Yodfat ................ A61M 5/1723
                                                               604/151
9,108,006 B2 *   8/2015   Jensen ................ A61M 5/1452
(Continued)

FOREIGN PATENT DOCUMENTS

CN       102458518 A       5/2012
CN       105473173 A       4/2016
(Continued)

*Primary Examiner* — James D Ponton
(74) *Attorney, Agent, or Firm* — Dickinson Wright PLLC (57) ABSTRACT

A medical device (100) includes an insulin pen (102), a pen needle (104) and a force sensor (106). The device also includes a microprocessor (206) to receive a signal from the force sensor (106). Audible and/or visual indicators (218, 220) provide feedback to a user to encourage proper injection technique. The device may also include an adaptor assembly comprising a sensor housing (306) and a first sensor (304) within the sensor housing, and a transfer needle assembly (308), the transfer needle assembly providing a connection (310) for a pen needle, and providing a fluid conduit between the pen needle (312) and the insulin pen (302). A second force sensor (314) is associated with a thumb button of the insulin pen (302).

11 Claims, 8 Drawing Sheets

(52) U.S. Cl.
CPC . *A61M 2205/581* (2013.01); *A61M 2205/583* (2013.01); *A61M 2205/587* (2013.01); *A61M 2205/8206* (2013.01); *A61M 2205/8262* (2013.01)

(58) Field of Classification Search
CPC ........ A61M 2205/332; A61M 2205/52; A61M 2205/581; A61M 2205/583; A61M 2205/587; A61M 2205/8206; A61M 2205/8262
See application file for complete search history.

(56) References Cited

U.S. PATENT DOCUMENTS

| | | | |
|---|---|---|---|
| 9,457,147 B2* | 10/2016 | Green | A61M 5/178 |
| 2010/0049126 A1 | 2/2010 | Bronfeld et al. | |
| 2014/0005950 A1 | 1/2014 | Groeschke et al. | |
| 2015/0302779 A1 | 10/2015 | Edwards et al. | |
| 2016/0157816 A1 | 6/2016 | Denny | |
| 2016/0193428 A1* | 7/2016 | Perthu | A61M 5/3287 604/506 |
| 2016/0361545 A1* | 12/2016 | Kaula | A61N 1/37241 |
| 2017/0049965 A1* | 2/2017 | Baker | A61M 5/31571 |
| 2017/0136185 A1* | 5/2017 | Rios | A61M 5/31511 |

FOREIGN PATENT DOCUMENTS

| | | |
|---|---|---|
| EP | 2 190 506 | 6/2010 |
| JP | 2014516599 A | 7/2014 |
| JP | 2016512144 A | 4/2016 |
| WO | 2009024562 A1 | 2/2009 |
| WO | 2012046199 A1 | 4/2012 |
| WO | 2016064916 A1 | 4/2016 |

* cited by examiner

United States Patent US 11,744,949 B2

SYSTEM AND METHOD FOR DETECTING APPLIED FORCE DURING INJECTION

Described herein is a system and method to detect and indicate forces applied to the skin surface during medicament injection for development of proper injection technique and facilitation of accurate needle insertion depth. Alternative embodiments incorporate an additional sensor to capture force applied to pen system injector button during dose administration.

BACKGROUND OF THE INVENTION

A majority of patients managing diabetes utilize syringe or pen devices for insulin administration and rely on proper injection technique and device performance for consistent delivery to the subcutaneous tissue space. Improper technique causing discomfort/pain may affect adherence to therapy. Poor technique leading to incomplete delivery of full dose (leakage), intradermal (shallow) or intramuscular (deep) delivery, and injection into lipohypertrophic tissue leads to inconsistent glycemic control and contributes to short and long term diabetes-related complications. Self-injection instruction is often only provided at the onset of treatment; consequently technique development is highly patient dependent which may result in sub-optimal methods due to psychological or physical barriers. Parents and caregivers performing injections are at a distinct disadvantage as direct sensory feedback is not possible.

Current injection systems do not provide information to the user regarding appropriate application force. Also mechanical relationships between pen needle hub, application force, and required injection depth exist necessitating the need for this type of information.

SUMMARY OF THE INVENTION

Embodiments of the invention provide a practical tool to diabetes and other medical educators, caregivers, and patients for development and maintenance of proper injection technique to promote consistent needle depth placement within the target tissue space. Systems according to an exemplary embodiment further provide a meaningful way to develop optimized injection devices (pen, autoinjectors, pen needles, syringes) by measuring and understanding applied insertion/application forces. Embodiments of the invention provide a clinically useful tool to measure and equate application forces to system function, patient acceptability, preference, and other human factors. Lastly by use of feedback control loops embodiments of the invention can facilitate appropriate use by either signaling when appropriate force is being applied to the device (e.g. by light, sound, or vibration indicators) or alternatively create a lock-out preventing use until system forces are in an appropriate range.

BRIEF DESCRIPTION OF THE DRAWING FIGURES

Embodiments of the present invention shall be described in connection with the appended drawings, in which.

Throughout the drawings, like reference numbers should be understood to refer to like elements, features and structures.

DETAILED DESCRIPTION OF EXEMPLARY EMBODIMENTS

Exemplary embodiments of the invention will now be described with reference to the appended drawing figures. It should be appreciated that the embodiments described herein are merely exemplary, and serve to illustrate to those of ordinary skill in the art how to make and use embodiments of the invention, but various changes and modifications may be made to the embodiments described herein without departing from the scope and spirit of the invention.

Figure 1A:
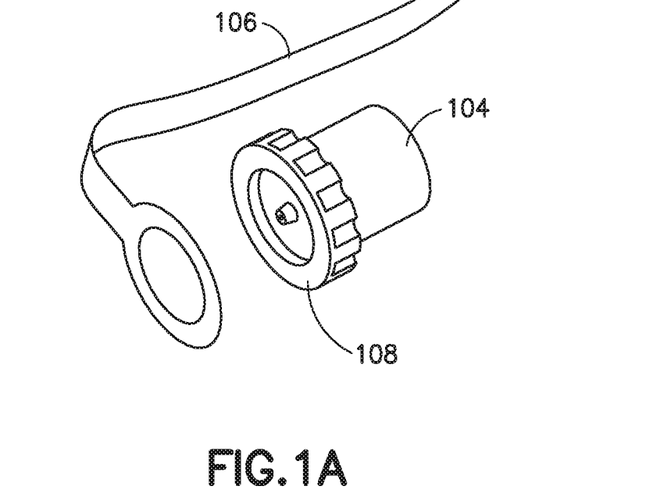
FIG. 1A is an exploded view of a first embodiment of the invention.
Figure 1B:
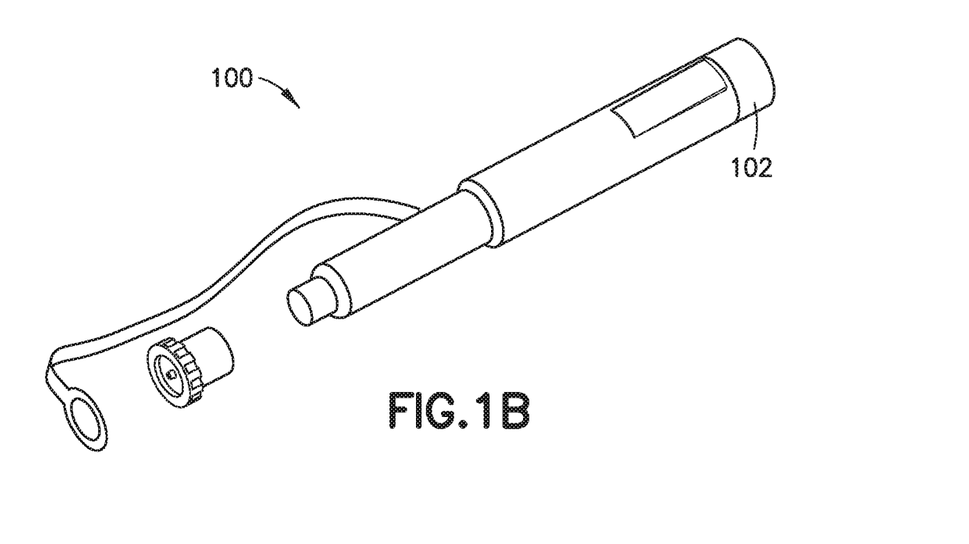
FIG. 1B is a detail view of a force sensor on the pen needle hub of FIG. 1A.

As illustrated in FIGS. 1A and 1B, a first embodiment of the invention is a device 100 comprising an insulin pen 102 with a pen needle 104 and a force sensor 106. Force sensor 106 is preferably arranged on the pen needle 104 hub face 108. When the insulin pen is used, the pen needle 104 is pressed against a skin surface, and the force sensor 106 converts changes in physical stimulus to electrical signals. The electrical signals are preferably conditioned and translated into mechanical quantities such as force values, by signal conditioning circuitry or the like, and transferred to a microcontroller where the force values may serve as input to an algorithm or process.

Figure 2:
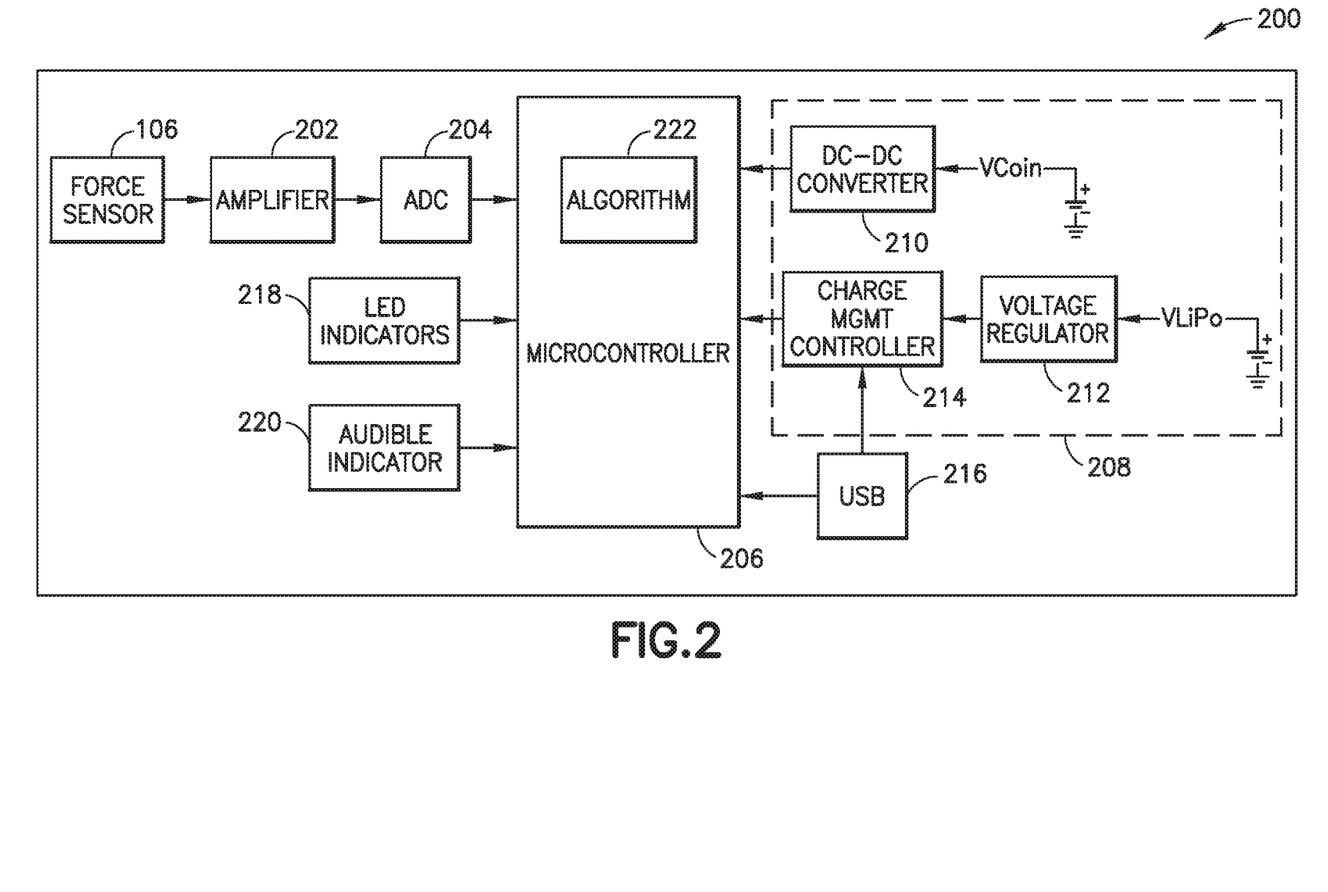
FIG. 2 is a block diagram of a signal processing circuit according to an exemplary embodiment of the invention.

FIG. 2 illustrates an exemplary block diagram of a processing circuit according to an embodiment of the invention. The processing circuit is preferably incorporated physically within the device 100 illustrated in FIGS. 1A and 1B, but those or ordinary skill in the art will readily appreciate that one or more of the components of the processing circuit described herein could be located in a separate device. The processing circuit 200 of FIG. 2 preferably includes force sensor 106, a signal amplifier 202 to amplify the raw signal received from the force sensor 106, an analog to digital converter 204, and a microcontroller 206 that receives a converted digital signal representing force values from the force sensor. The processing circuit also preferably includes a power supply 208, that preferably includes a DC-to-DC converter 210 for supplying power to the microcontroller 206 from a coin battery, or the like. The power supply 208 also preferably includes a rechargeable battery, such as a LiPO battery (not shown) and an associated voltage regulator 212 and charge management controller 214. Preferably, the processing circuit also includes a USB port 216, or the like, for connecting the processing circuit 200 to other devices and for charging the rechargeable battery. The processing circuit 200 preferably also includes visual indicators, such as LED indicators 218 and audible indicators 220 for outputting indications to a user.

Microcontroller 206 preferably includes or is associated with a memory 222 containing program instructions for execution. The program instructions advantageously may be provided to follow a set of rules based on the data received from the force sensor, and to provide feedback based on the measured application force to the caregiver via visual and/or audible indications.

Figure 3:
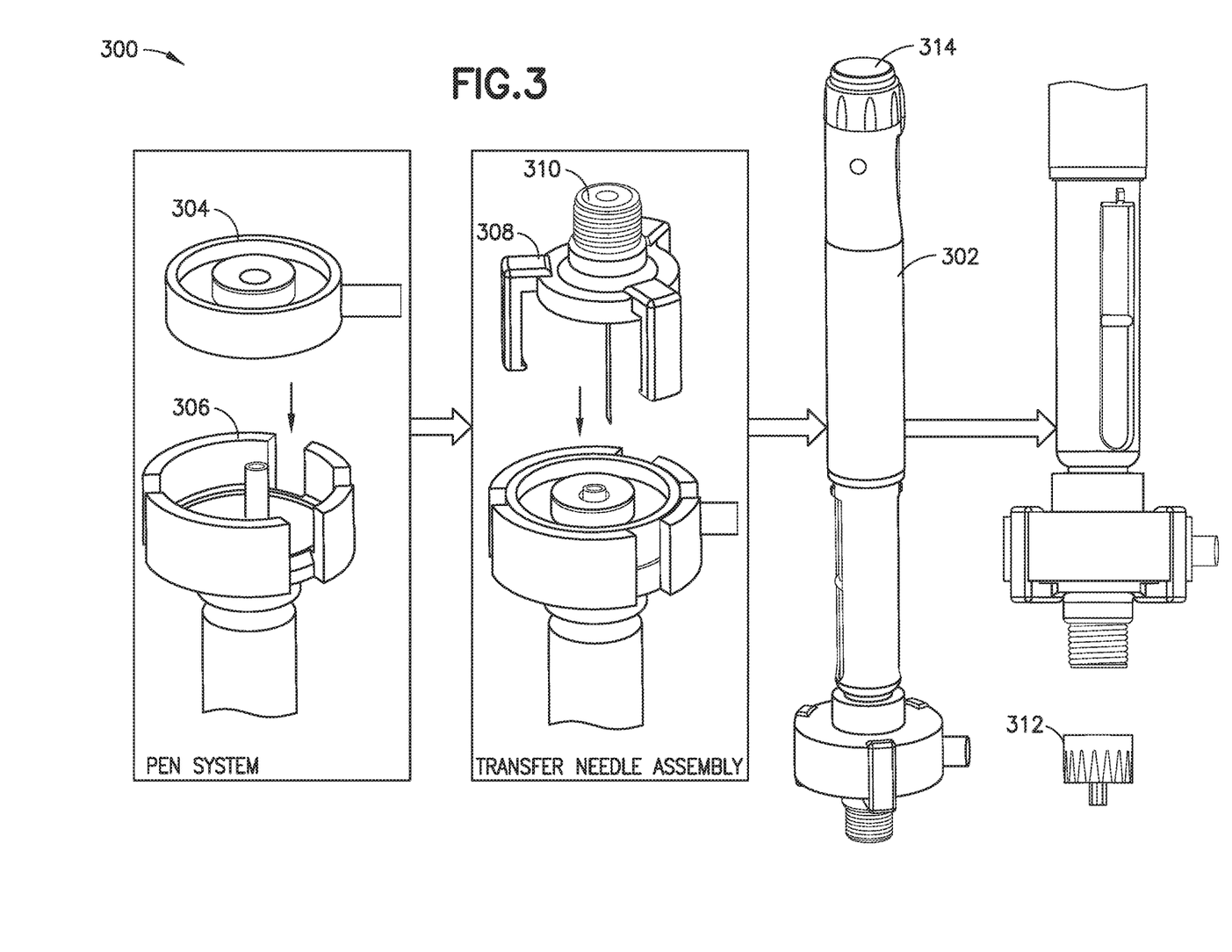
FIG. 3 illustrates another embodiment of the invention with two force sensors.
Figure 4A:
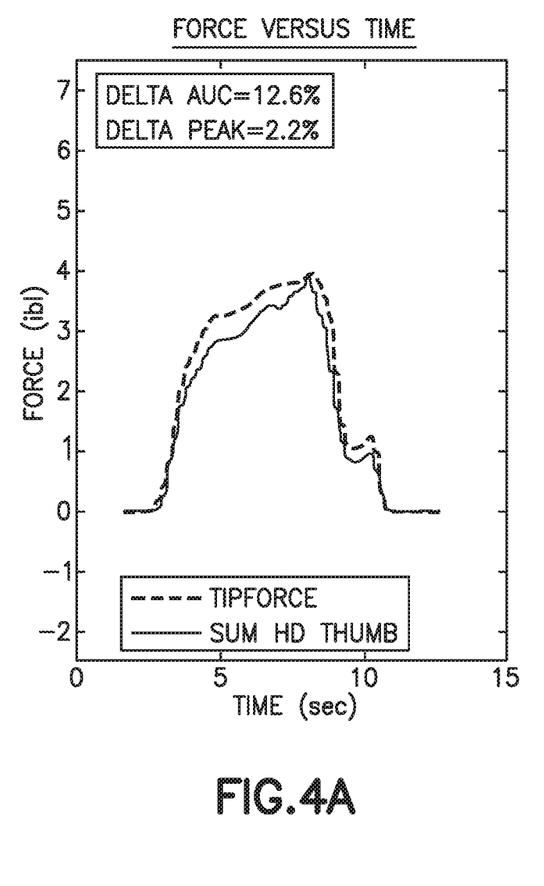
FIGS. 4A-4I are charts of force over time illustrating thumb and skin application force.
Figure 4B:
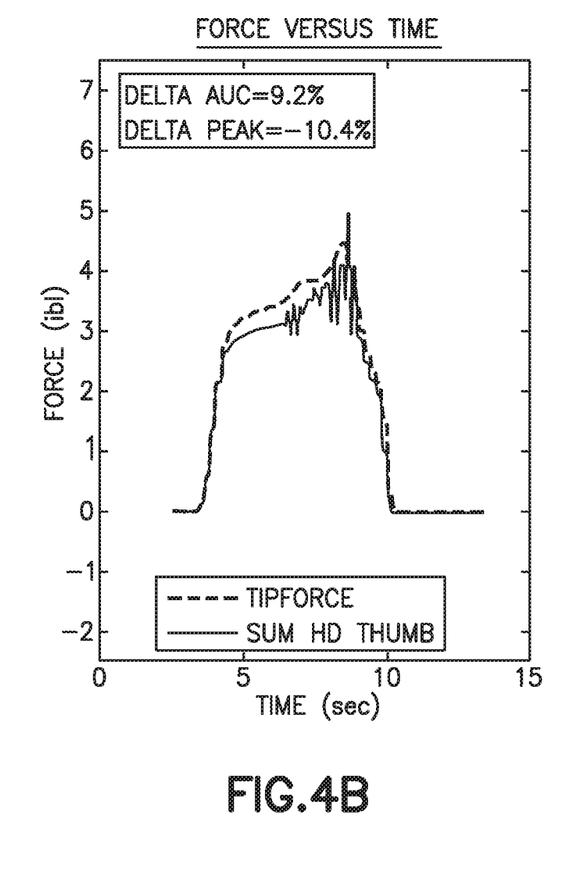
Figure 4C:
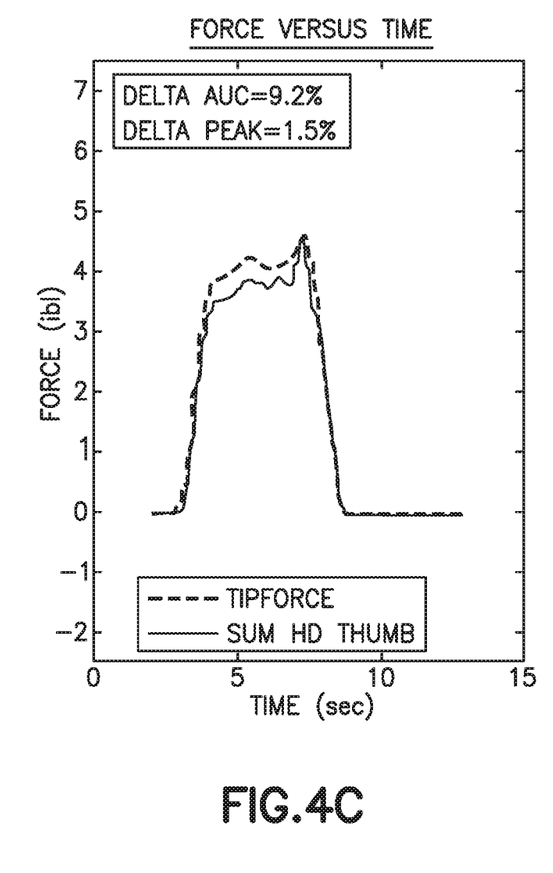
Figure 4D:
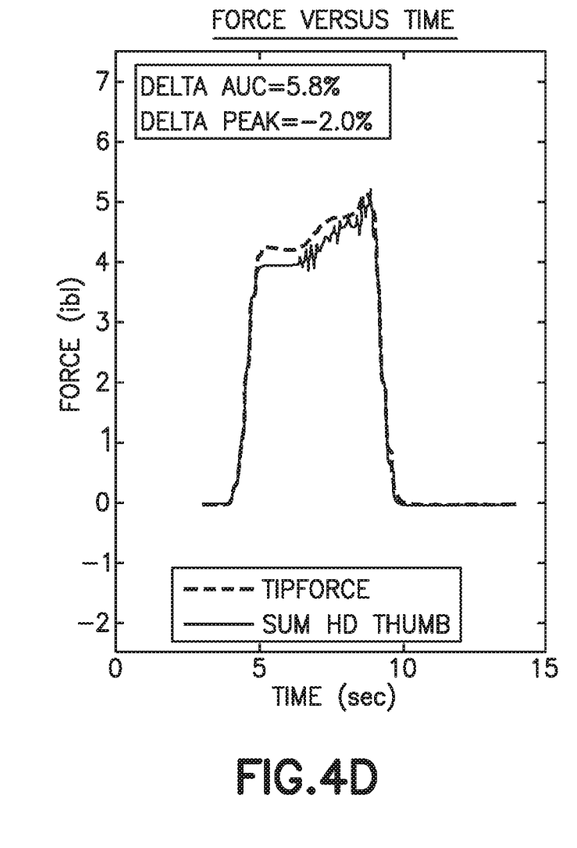
Figure 4E:
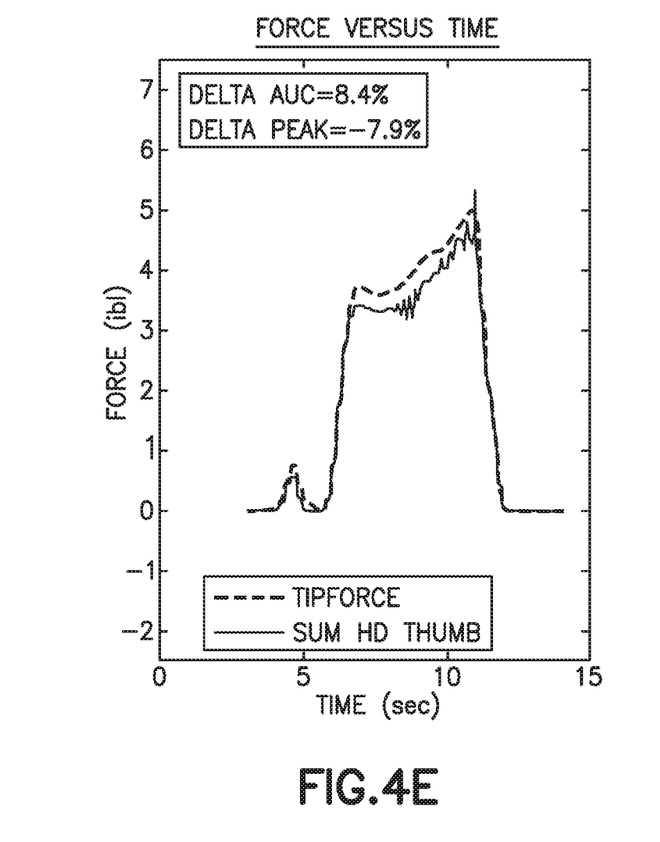
Figure 4F:
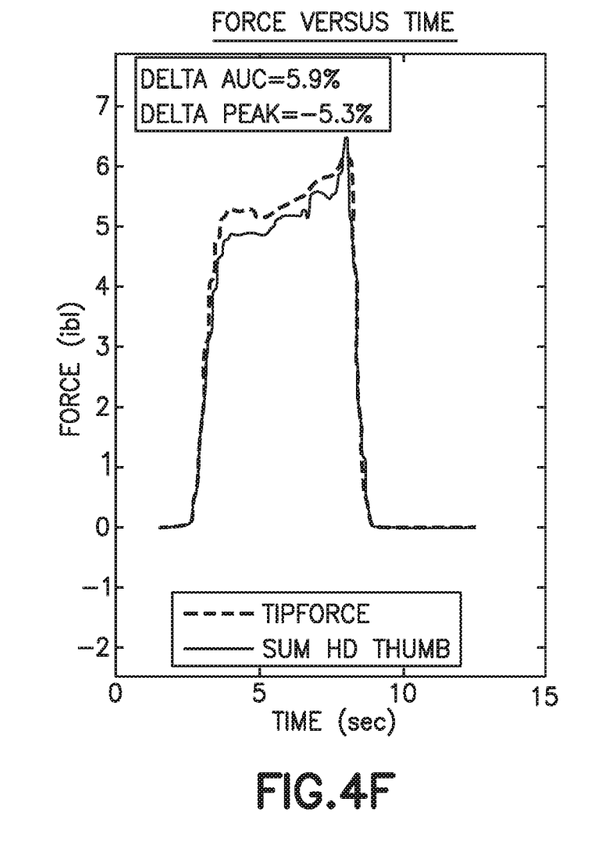
Figure 4G:
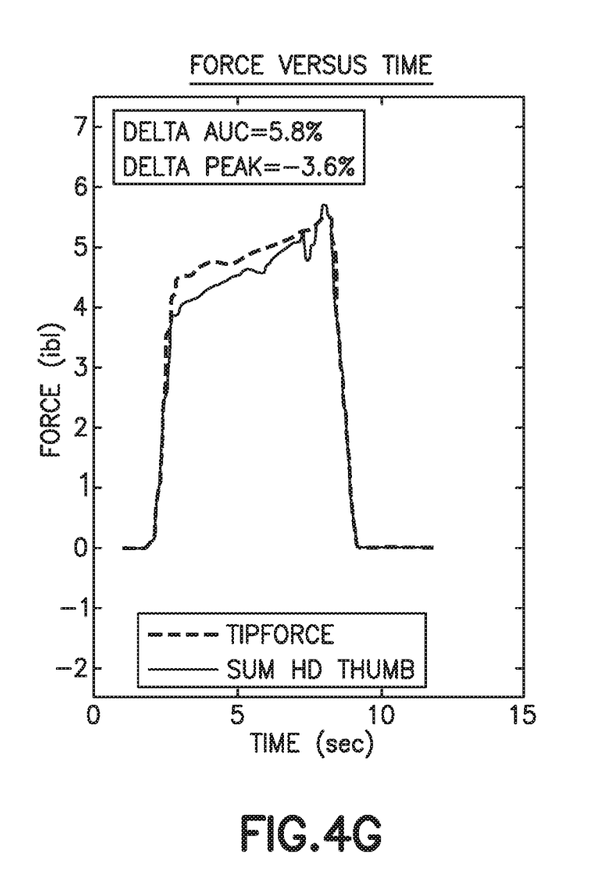
Figure 4H:
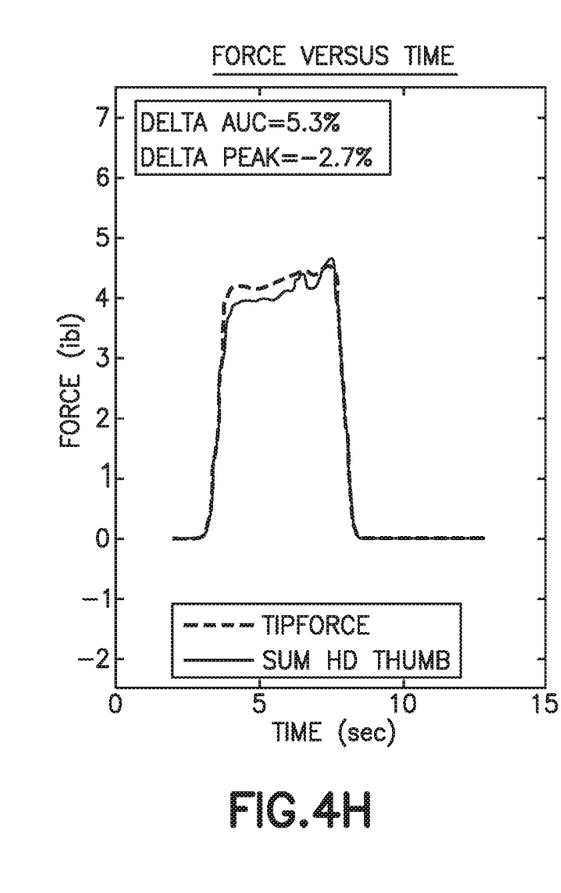
Figure 4I:
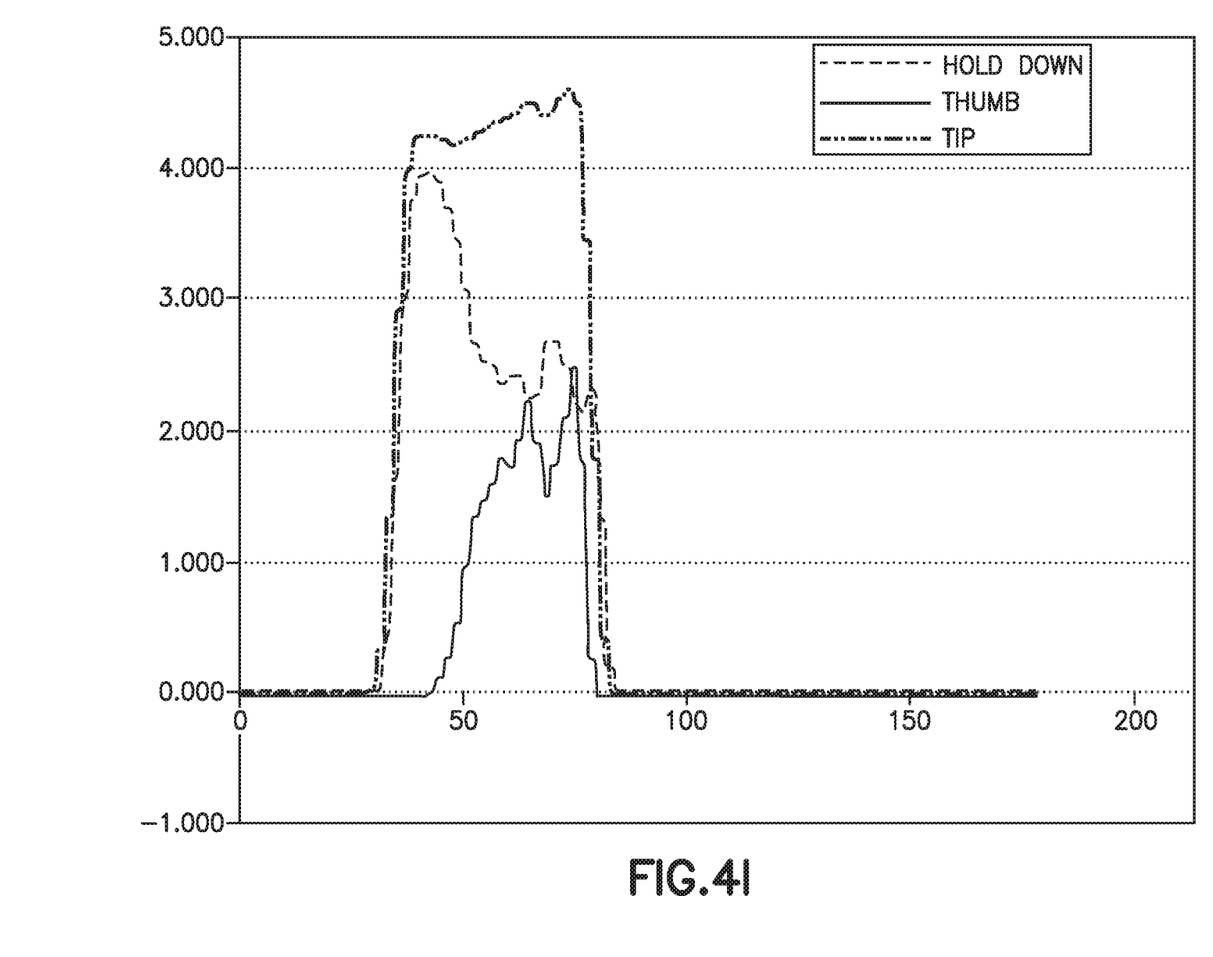

A second exemplary embodiment is illustrated in FIG. 3. The second embodiment is similar to the first, except that the device 300 includes two load sensors rather than one. This embodiment comprises an adapter assembly 300 that may be incorporated onto the end of any standard insulin pen 302. The assembly 300 comprises a force sensor 304 such as a donut shaped load cell, a sensor housing 306, and a transfer needle assembly 308. The adapter assembly 300 preferably threads onto a standard insulin pen, and provides a connection 310 for a pen needle 312. The force sensor 304 measures force applied to the skin surface during the injection procedure. The device 300 also includes a load sensor 314 that is associated with a thumb button 308 to measure a force applied to deliver medicament through the pen system. Processing circuitry and power supply may be incorporated into the adapter assembly, or connections may be provided to an external device that houses those components. In this manner, injection forces may be measured, and feedback provided to the user of any standard insulin pen.

FIGS. 4A-4I illustrate data recorded from a device according to the second embodiment. As illustrated, two load sensors were incorporated into the device, one on the thumb button, and one within the connector adaptor. Force measured over time by the two sensors is plotted in the figure. As illustrated, for this particular injection, the force applied to the skin is immediately measured and held to a semi-steady level, followed by measurement of thumb force required to deliver injectate from the pen system into the injection site. Upon completion of fluid delivery applied thumb force is halted. The device is held to the skin surface post-fluid delivery for 5-10 seconds to minimize leakage from the injection site. At the end of the injection procedure, the insulin pen is withdrawn from the user.

As will be appreciated by those of ordinary skill in the art, by recording the forces present in the insulin pen, or its components, during an injection, analysis of the injection may be undertaken, and feedback derived and provided to the user. For example, such data would reveal of the user is not using enough force, or not holding the insulin pen to the injection site for a long enough duration after the thumb button is pressed.

A preferred embodiment of the device has a force sensor integrated into or on the pen needle hub face. Electrical connections are provided within pen needle hub to provide power to the force sensor, and force signals are acquired for further processing. The processing circuit and power supply are preferably provided inside the pen system body.

A second embodiment includes a force sensor integrated into or on the pen needle hub, with flex circuit leads that are adapted to be connected to a separate housing external to the insulin pen. The power supply and processing circuitry are preferably located within the external housing. The external housing is adapted to be fit over an insulin pen as an add-on device.

As will be appreciated by those of ordinary skill in the art, any of the embodiments described herein may incorporate circuit components that enable data transfer over wired or wireless medium to a durable medium such as a CPU, tablet, phone, and/or watch with associated software application for data visualization and storage.

Those of ordinary skill in the art will also appreciate that although embodiments of the invention have been described in connection with a pen needle device, any suitable injection or drug delivery system requiring direct contact with the skin or other physiologic surfaces could take advantage of the principles and features outlined herein.

Finally, those of ordinary skill in the art will appreciate that modifications to the disclosed embodiments are possible without departing from the scope of the invention as defined in the claims and their equivalents, and that the features of different embodiments and claims may be combined with each other as long as they do not contradict each other.

The invention claimed is:

1. A medical device comprising:
an insulin pen with a pen needle attached thereto,
a first force sensor arranged on a hub face of the pen needle,
a second force sensor arranged on a thumb button of the insulin pen,
a microcontroller that receives a first signal from the first force sensor and a second signal from the second force sensor during an injection; wherein the microcontroller is programmed to determine, from the first and second signals received during the injection, a force over time profile, and based on the determined force over time profile, whether or not the injection was properly administered; and
at least one of an audible indicator and a visual indicator controlled by the microcontroller.

2. The medical device of claim 1, further comprising an amplifier to amplify an analog signal of at least one of the first and second force sensors, and an analog to digital converter to convert the amplified signal to digital.

3. The medical device of claim 1, further comprising a power supply supplying power to the microcontroller.

4. The medical device of claim 3, further comprising a voltage regulator to regulate power from the power supply, and a charge management controller to regulate the charge of a battery.

5. The medical device of claim 4, wherein the battery is a rechargeable battery.

6. The medical device of claim 1, further comprising a USB port for connecting the microcontroller to an external device, and for receiving power to charge a battery.

7. The medical device of claim 1, further comprising a memory containing program instructions to follow rules based on data received from the first and second force sensors, and to provide feedback via the at least one indicator based on an applied force measured by the force sensor.

8. A medical device comprising:
an insulin pen for receiving a pen needle at a pen needle attachment portion;
an adapter assembly that attaches to the attachment portion of the insulin pen, and which receives the pen needle on an opposite end of the adapter assembly;
the adapter assembly comprising a first force sensor, a sensor housing and a transfer needle assembly that provides a fluid conduit between the pen needle and the insulin pen;
a second force sensor associated with a thumb button of the insulin pen; and
a microprocessor that receives a first signal from the first force sensor and a second signal from a second force sensor during an injection; and wherein the microprocessor is programmed to determine, from the first and second signals received during the injection, whether or not the injection was properly administered.

9. The medical device of claim 8, further comprising a power supply.

10. The medical device of claim 8, wherein the first force sensor measures a force of the pen needle against skin, and the second force sensor measures a force applied to the thumb button.

11. The medical device of claim 8, further comprising at least one of an audible indicator and a visual indicator.

\* \* \* \* \*